(12) United States Patent
Zhao et al.

(10) Patent No.: US 11,786,568 B2
(45) Date of Patent: Oct. 17, 2023

(54) **STRAIN OF CAUCASUS YOGHURT *LACTOBACILLUS* MSR101 AND USE THEREOF**

(71) Applicant: SHENZHEN UNIVERSITY, Guangdong (CN)

(72) Inventors: Liqing Zhao, Guangdong (CN); Muhammad Shahid Riza Rajoka, Guangdog (CN)

(73) Assignee: SHENZHEN UNIVERSITY, Guangdong (CN)

( * ) Notice: Subject to any disclaimer, the term of this patent is extended or adjusted under 35 U.S.C. 154(b) by 0 days.

(21) Appl. No.: 17/288,315

(22) PCT Filed: Mar. 18, 2020

(86) PCT No.: PCT/CN2020/079861
§ 371 (c)(1),
(2) Date: Apr. 23, 2021

(87) PCT Pub. No.: WO2020/228410
PCT Pub. Date: Nov. 19, 2020

(65) Prior Publication Data
US 2022/0056401 A1   Feb. 24, 2022

(30) Foreign Application Priority Data
May 10, 2019  (CN) .......................... 201910388000.6

(51) Int. Cl.
| | | |
|---|---|---|
| *A61K 35/747* | (2015.01) | |
| *A61P 3/00* | (2006.01) | |
| *A61K 35/00* | (2006.01) | |
| *C12N 1/24* | (2006.01) | |
| *C12R 1/225* | (2006.01) | |

(52) U.S. Cl.
CPC ............ *A61K 35/747* (2013.01); *A61K 35/00* (2013.01); *A61P 3/00* (2018.01); *C12N 1/24* (2013.01); *A61K 2035/115* (2013.01); *C12R 2001/225* (2021.05)

(58) Field of Classification Search
CPC ........ A61P 3/00; A61P 3/06; A61K 2035/115; A61K 35/747; C12R 2001/225
See application file for complete search history.

(56) References Cited

FOREIGN PATENT DOCUMENTS

| CN | 104818230 A | 8/2005 | | |
|---|---|---|---|---|
| CN | 104073455 A | 10/2014 | | |
| CN | 104560793 A | * | 4/2015 | ............ A23C 9/127 |
| CN | 107058161 A | * | 8/2017 | ........... A23C 9/1234 |
| CN | 107058161 A | 8/2017 | | |
| CN | 110106113 A | 8/2019 | | |

OTHER PUBLICATIONS

Kim, D et al. Dual function of Lactobacillus kefiri DH5 in preventing high-fat-diet-induced obesity: direct reduction of cholesterol and upregulation of PPAR-alpha in adipose tissue. Mol. Nutr. Food Res. 2017. 61: 11. 12 pages. (Year: 2017).*
Zheng, Y et al. Probiotic properties of Lactobacillus strains isolated from Tibetan kefir grains. PLoS One. 2013. 8(7): e69868. 8 pages. (Year: 2013).*
NCBI Blast:ref|NZ_CP029971.1| [online], 2023 [retrieved on Apr. 5, 2023]. Retrieved from the Internet: <URL: https://blast.ncbi.nlm.nih.gov/Blast.cgi> (Year: 2023).*
NCBI Blast:gb|KC155629.1| [online], 2023 [retrieved on Apr. 5, 2023]. Retrieved from the Internet: <URL: https://blast.ncbi.nlm.nih.gov/Blast.cgi#> (Year: 2023).*
BLAST. [online] 2023 [retrieved on Jun. 28, 2023]. Retrieved from the Internet: <URL: https://blast.ncbi.nlm.nih.gov/Blast.cgi>) (Year: 2023).*
Applicant: Shenzhen University; Title: "Lactobacillus Kefiri MSR101 and Application Thereof"; PCT International Application No. PCT/CN2020/079861 filed Mar. 18, 2020; PCT International Search Report; dated Jun. 24, 2020; 10 pgs.
Zhao Tong, et al.; "Analysis of Probiotic Characteristics of Lactobacillus kefiri KL22[J]"; Science and Technology of Food Industry, 2019, 40(9): 115-120. doi: 10.13386/j.issn1002-0306.2019.09.021.
Chen XiaoYong, et al.;"In vitro screening of lactic acid bacteria with probiotic properties from traditional fermented Yak yogurt"; College of Food Science, Southwest University, Chongqing 400715, China; Journal article: Food and Fermentation Industries 2016 vol. 42 No. 4 pp. 85-90.
Tong Zhao, et al.; "Study on the characteristics of L. Kefir KL22"; China Food Additives, No. 10, Oct. 31, 2018; ISSN: 1006-2513.
Zhuqing Xing et al.; "In vitro and in vivo evaluation of the probiotic attributes of Lactobacillus kefiranofaciens XLIO isolated from Tibetan kefir grain"; Appl Microbiol Biot, vol. 101, No. 6, Mar. 31, 2017, ISSN: 0175-7598; 11 pgs.

* cited by examiner

*Primary Examiner* — David W Berke-Schlessel
*Assistant Examiner* — Susan E. Fernandez
(74) *Attorney, Agent, or Firm* — Tarolli, Sundheim, Covell & Tummino, LLP

(57) ABSTRACT

Provided is *Lactobacillus kefiri* MSR101, having the accession member being CGMCC No. 17506. The strain has acid resistance, bile salt resistance, resistance to phenol, antibiotic resistance, antioxidant activity, cell surface hydrophobicity, adhesion to intestinal epithelial cells, and a cholesterol-lowering function.

1 Claim, 2 Drawing Sheets
Specification includes a Sequence Listing.

SEQUENCE LISTING

<160> NUMBER OF SEQ ID NOS: 3

<210> SEQ ID NO 1
<211> LENGTH: 1032
<212> TYPE: DNA
<213> ORGANISM: Artificial Sequence
<220> FEATURE:
<223> OTHER INFORMATION: Sequence of 16S rDNA

<400> SEQUENCE: 1

```
gcttggcgtc gtgctataca tgcaagtcga acgcgtttcc gttattgatt ttagagtgtt      60
gcatttgaat gatttaacac gaaacgagtg gcgaactggt gagtaacacg tgggtacctg     120
cccttgaagt aggggataac acttggaaac aggtgctaat accgtataac aaccaaaacc     180
acatggtttt ggtttaaaag atggcttcgg ctatcacttt aggatggacc cgggcgtatt     240
```

```
agcttgttgg taaggtaatg gcctaccaag gcaatgatac gtagccgacc tagagggtaa    300
tcggccacat tgggactgag acacggccca aactcctacg ggaggcaggt agggaatctt    360
ccacaatgga cgaaagtctg atggagcaac gccgcgtgag tgatgaaggg tttcggctcg    420
taaaactctg ttgttggaga agaacaggtg tcagagtaac tgttgacatc ttgacggtat    480
ccaaccagaa agccacggct aactacgtgc cagcagccgc ggtaatacgt aggtggcaag    540
cgttgtccgg atttattggg cgtaaagcga gcgcaggcgg ttcttaggtc tgatgtgaaa    600
gccttcggct taaccggaga agtgcatcgg aaaccaggag acttgagtgc agaagaggac    660
agtggaactc catgtgtagc ggtgaaatgc gtagatatat ggaagaacac cagtggcgaa    720
ggcggctgtc tggtctgtaa ctgacgctga ggctcgaaag catgggtagc gaacaggatt    780
agataccctg gtagtccatg ccgtaaacga tgagtgctaa gtgttggagg gtttccgccc    840
ttcagtgctg cagctaacgc attaagcact ccgcctgggg agtacgaccg caaggttgaa    900
actcaaagga attgacgggg gcccgcacaa gcggtgagca tgtgtttaat tcgatgctac    960
gcgaagacct taccaggtct tgacatcttt ctcctatttc tgtcaccttta gacggctggt   1020 ccccgaaggt ta                                                        1032

<210> SEQ ID NO 2
<211> LENGTH: 20
<212> TYPE: DNA
<213> ORGANISM: artificial sequence
<220> FEATURE:
<223> OTHER INFORMATION: Forward primer for amplifying 16S rDNA

<400> SEQUENCE: 2
agagtttgat cctggctcag                                                  20

<210> SEQ ID NO 3
<211> LENGTH: 20
<212> TYPE: DNA
<213> ORGANISM: artificial sequence
<220> FEATURE:
<223> OTHER INFORMATION: Reverse primer for amplifying 16S rDNA

<400> SEQUENCE: 3
ccgtcaattc ctttgagttt                                                  20
```

STRAIN OF CAUCASUS YOGHURT *LACTOBACILLUS* MSR101 AND USE THEREOF

CROSS REFERENCE TO RELATED APPLICATION

This disclosure claims the priority of Chinese Patent Application No. CN201910388000.6 entitled "Strain of Caucasus yoghurt *Lactobacillus* MSR101 and use thereof" filed with the China National Intellectual Property Administration on May 10, 2019, which is incorporated herein by reference in its entirety.

TECHNICAL FIELD

This disclosure belongs to the technical field of *Lactobacillus*, and specifically relates to a strain of *Lactobacillus kefiri* MSR101 and its use.

BACKGROUND

Probiotic microorganisms are "living microorganisms" that can bring various health benefits to the host, including regulation of immune system, rearrangement of gastrointestinal microbiota and inhibition of growth of harmful microorganisms (Maleki Kakelar et al., 2019). Lactic acid bacteria are the most important probiotics and are compatible with human digestive system because of their natural resistance to low pH and high bile salt conditions (Shehata et al., 2016, Riaz Rajoka et al., 2018).

In the past 10 years, probiotics have become a research hotspot in the field of lactic acid bacteria, including *Lactobacillus* and *Bifidobacterium*. (Bao et al., 2010). Recently, there has been a new understanding of the amount of consumption of *Lactobacillus* strains isolated from traditional Chinese dairy products with various health-promoting effects. In order to provide the host with necessary conditions far health, the isolated *Lactobacillus* strains must have the ability to pass through the physical and chemical barriers of the gastrointestinal tract (Ramos et al., 2018). In addition, as a probiotic, the *Lactobacillus* strain must have the ability to survive in sufficient numbers during the production and storage of the intended products.

SUMMARY OF THE INVENTION

In view of the problems in the background technology, the present disclosure provides a strain of *Lactobacillus kefiri* MSR101 and its use. The *lactobacillus* of the present disclosure has acid resistance, bile salt resistance, resistance to phenol, antibiotic resistance, antioxidant activity resistance, cell surface hydrophobicity, adhesion to intestinal epithelial cells and cholesterol-lowering function.

The present disclosure provides a strain of *Lactobacillus kefiri* MSR101 deposited with the China General Microbiological Culture Collection Center (CGMCC) under the accession number of CGMCC No. 17506.

The present disclosure also provides the use of *Lactobacillus kefiri* MSR101 described in the above technical scheme in resistance to high bile salt.

The present disclosure also provides the use of *Lactobacillus kefiri* MSR101 described in the above technical scheme in phenol tolerance.

The present disclosure also provides the use of *Lactobacillus kefiri* MSR101 described in the above technical scheme in anti-oxidation.

The present disclosure also provides the use of *Lactobacillus kefiri* MSR101 described in the above technical scheme in lowering concentration of cholesterol.

The present disclosure also provides the use of *Lactobacillus kefiri* MSR101 described in the above technical scheme in resistance to penicillin, ampicillin, streptomycin and tetracycline.

The present disclosure also provides the use of *Lactobacillus kefiri* MSR101 in treatment of hypercholesterolemia.

The present disclosure also provides the use of *Lactobacillus kefiri* MSR101 described in the above technical scheme in treatment of high bile salt diseases.

Beneficial Effects

The present disclosure provides a strain of *Lactobacillus kefiri* MSR101. The *Lactobacillus* of the present disclosure has acid resistance, bile salt resistance, resistance to phenol, antibiotic resistance, antioxidant activity resistance, cell surface hydrophobicity, adhesion to intestinal epithelial cells and cholesterol-lowering functions. The test results showed that the *Lactobacillus kefiri* MSR101 strain entered into a stationary phase after 48 hours of culture and the yield of EPS was up to 753 mg/L. The *Lactobacillus kefiri* MSR101 strain showed high hydrophobicity (70%) to xylene. The highest adhesion rate of HT-29 to intestinal epithelial cells was 34.4%, the clearance rate for superoxide anion free radicals was 65.5%, the clearance rate for DPPH free radicals was 43.3%, and the removal rate for cholesterol was 26.2%.

STATEMENT ON BIOLOGICAL DEPOSIT

Figure 1:
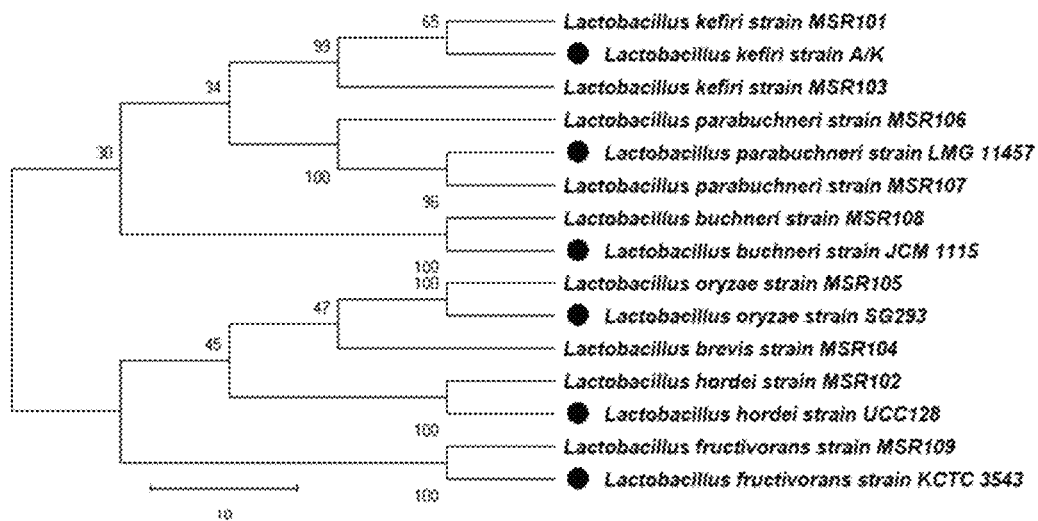
FIG. 1 is a diagram of the results for phylogenetic tree analysis provided by the present disclosure.

*Lactobacillus kefiri* MSR101. This strain is deposited in the China General Microbiological Culture Collection Center (CGMCC) under the terms of the Budapest Treaty, the address is No. 3, Suite 1, Beichen West Road, Chaoyang District, Beijing, Institute of Microbiology, Chinese Academy of Sciences, the accession number is CGMCC No. 17506, and the deposit date is 2019 Apr. 1.

DETAILED DESCRIPTION OF THE EMBODIMENTS

The present disclosure will be further described below in conjunction with embodiments and drawings.

The present disclosure provides a strain of *Lactobacillus kefiri* MSR101 having an accession number of CGMCC No. 17506.

*Lactobacillus kefiri* MSR101 is an anaerobic, gram-positive bacterium, it is a rod-shaped bacterium.

The *Lactobacillus kefiri* MSR101 of the present disclosure is gram-positive, catalase-negative, rod-shaped and mesophilic. The 16s rRNA gene sequence is shown in SEQ ID NO. 1
a) GCTTGGCGTCGTGCTATACATGCAAGTCGAACGCGTTTCCGTTATT

GATTTTAGAGTGTTGCATTTGAATGATTTAACACGAAACGAGTGGCGAA

CTGGTGAGTAACACGTGGGTACCTGCCCTTGAAGTAGGGGATAACACTT

GGAAACAGGTGCTAATACCGTATAACAACCAAAACCACATGGTTTTGGT

TTAAAAGATGGCTTCGGCTATCACTTTAGGATGGACCCGGGCGTATTAG

CTTGTTGGTAAGGTAATGGCCTACCAAGGCAATGATACGTAGCCGACCT

AGAGGGTAATCGGCCACATTGGGACTGAGACACGGCCCAAACTCCTACG

GGAGGCAGGTAGGGAATCTTCCACAATGGACGAAAGTCTGATGGAGCAA

CGCCGCGTGAGTGATGAAGGGTTTCGGCTCGTAAAACTCTGTTGTTGGA

GAAGAACAGGTGTCAGAGTAACTGTTGACATCTTGACGGTATCCAACCA

GAAAGCCACGGCTAACTACGTGCCAGCAGCCGCGGTAATACGTAGGTGG

CAAGCGTTGTCCGGATTTATTGGGCGTAAAGCGAGCGCAGGCGGTTCTT

AGGTCTGATGTGAAAGCCTTCGGCTTAACCGGAGAAGTGCATCGGAAAC

CAGGAGACTTGAGTGCAGAAGAGGACAGTGGAACTCCATGTGTAGCGGT

GAAATGCGTAGATATATGGAAGAACACCAGTGGCGAAGGCGGCTGTCTG

GTCTGTAACTGACGCTGAGGCTCGAAAGCATGGGTAGCGAACAGGATTA

GATACCCTGGTAGTCCATGCCGTAAACGATGAGTGCTAAGTGTTGGAGG

GTTTCCGCCCTTCAGTGCTGCAGCTAACGCATTAAGCACTCCGCCTGGG

GAGTACGACCGCAAGGTTGAAACTCAAAGGAATTGACGGGGGCCCGCAC

AAGCGGTGAGCATGTGTTTAATTCGATGCTACGCGAAGACCTTACCAGG

TCTTGACATCTTTCTCCTATTTCTGTCACCTTAGACGGCTGGTCCCCGA

AGGTTA.

The sequence shows that it is 99% similar to the sequence of known species available in the NCBI database, and the sequence is deposited in the Gene Bank under the accession number MK491609. *Lactobacillus kefiri* MSR101 of the present disclosure has beneficial effects in aspects of antibiotic sensitivity, tolerance under intestinal conditions (low pH, bile salt tolerance and 0.2% to 0.4% resistance to phenol), hydrophobicity, antioxidant ability, reduction of cholesterol, and adhesion to HT-29, etc. The *Lactobacillus kefiri* MSR101 is resistant to penicillin, ampicillin, streptomycin and tetracycline. In addition, it also exhibited adhesion (34.3%) and antioxidant activity (67%) to HT-29 cells and it showed a high survival rate (>80%) under gastrointestinal conditions.

The present disclosure also provides the use of *Lactobacillus kefiri* MSR101 described in the above technical scheme in the resistance to high bile salt. The strain of the present disclosure grows well under high bile salt conditions (0.3%, 0.5% and 1% bile (w/v)).

The present disclosure also provides the use of *Lactobacillus kefiri* MSR101 described in the above technical scheme in phenol tolerance. The strain of the present disclosure has good survival ability at a phenol concentration of 0.2% to 0.4%.

The present disclosure also provides the use of *Lactobacillus kefiri* MSR101 described in the above technical scheme in antioxidant. The strain of the present disclosure has antioxidant activity (67%).

The present disclosure also provides the use of *Lactobacillus kefiri* MSR101 described in the above technical scheme in lowering concentration of cholesterol. The cholesterol-lowering ability of the strain of the present disclosure is 26.2±0.6%.

The present disclosure also provides the use of *Lactobacillus kefiri* MSR101 described in the above technical scheme in resistance to penicillin, ampicillin, streptomycin and tetracycline.

The present disclosure also provides the use of *Lactobacillus kefiri* MSR101 in the treatment of hypercholesterolemia.

The present disclosure also provides the use of *Lactobacillus kefiri* MSR101 described in the above technical scheme in the treatment of high bile salt diseases.

The present disclosure will be further clarified below in conjunction with specific embodiments. These embodiments are implemented on the premise of the technical solution of the present disclosure. It should be understood that these embodiments are only used to illustrate the present disclosure and not to limit the scope of the present disclosure.

Example 1

Sampling

The experimental samples were traditional Chinese dairy products from the Tibet Autonomous Region of Qinghai Province, China. There were totally 20 samples, including yak milk (4), horse milk wine (5), cheese (4) and kefir grains (7). The samples were collected in sterile tubes and stored in a mini freezer at −15° C. The test was carried out in the laboratory immediately after receiving the sample.

Isolation and Identification of *Lactobacillus*

The samples were serially diluted in phosphate buffered saline (PBS, pH 7.2), and a small aliquot (50 μl) of each batch of diluted solution was spread on a de Man-Rogosa-Sharpe (Merck, China) MRSc agar plate supplemented with 0.05% L-cysteine. The plate were incubated anaerobically at 37° C. for 72 h. Colonies with different morphologies were selected and a new freshly prepared MRSc agar plate was re-streaked and counted for several generations, and a single colony was isolated and purified. All isolated strains were confirmed to be lactic acid bacteria by Gram staining and catalase rest, and the gram-positive and catalase-negative strains were all lactic acid bacteria. The identification of *Lactobacillus* isolates was performed by sequencing the 16S rDNA gene. Genomic DNA purification kit (TransGenBiotech Co., Ltd., Beijing, China) was used to extract total genomic DNA according to the instructions. The primers used to amplify the 16S rDNA sequence are forward 5"-AGAGTTTGATCCTGGCTC AG-3" (SEQ ID NO. 2) and reverse 5"-CCGTCAATTCCTTTGAGTTT-3" (SEQ ID NO. 3). In the Techne-TC 512 thermal cycler (UK), the fragments were amplified under the following conditions: 95° C., 1 min; 95° C., 30 s, 30 cycles; 55° C., 30 seconds, and finally 72° C., 5 min. The amplified fragments were screened on agarose gel and sequenced by Guangzhou IGE Biotechnology Co., Ltd. in Shenzhen, China. All obtained sequences were tested by the BLAST program (blast.ncbi.nlm.nih.gov/Blast.cgi). The sequence was stored in the gene bank. Sequence alignment was performed by ClustalW2 (www.ebi.ac.uk/Tool/mas/clustalw2/), and a phylogenetic tree was constructed by a neighbor joining method (Tamura et al., 2004) and a compound maximum likelihood method. Software of Mega 6.0 (megasoftware.net/) (Saitou and Nei, 1987) was used. The results showed that live kefir cells are one of the sources of *Lactobacillus*.

The results of the phylogenetic tree analysis are shown in FIG. 1. The phylogenetic tree is constructed on the basis of the 16S rRNA sequence. Genome probability is determined by the number of 1000 repeats and expressed as a percentage value. The filled circle indicates that the strain is from NCBI, and the open circle indicates that the isolated *Lactobacillus* strain was used for developmental tree construction.

Example 2

Survival Under Low pH and High Bile Salt Conditions

The survival ability of *Lactobacillus* at pH2.0, pH2.5, pH3.0 and pH6.5 (control group) was evaluated according to the method described by Lee et al., 2011. At the same time, using $MRS_c$ broth medium containing 0.3%, 0.5% and 1% bile (w/v), the bile salt tolerance of lactobacilli that survived for 3 hours under acidic conditions was measured according to the method by Sabir et al., 2010b. $MRS_c$ broth medium without bile salts was used as a control. According to formula (1), the resistance of lactobacilli to acidic conditions and bile salt conditions was evaluated by the counts on the $MRS_c$ agar plate.

Growth rate (%)=$(N_1/N_{10})\times 100$      Formula (1)

Among them, $N_1$ is the total number of live bacterial cells in the $MRS_c$ broth after treatment, and $N_0$ is the total number of live bacterial cells in the $MRS_c$ broth before treatment. The results showed that strains MSR101 grew well under the conditions of low pH (pH2.0, pH2.5, pH3.0) and high bile salt (0.3%, 0.5% and 1% bile (w/v)).

Example 3

Phenol Tolerance

The phenol tolerance determination was carried out by using a method as previously reported (Shehata et al., 2016), with a slight modification made. The 1% fraction of lactic acid bacteria was cultured for 24 hours and then inoculated into a MRsc fermentation solution supplemented with 0.2% and 0.4% phenol. A MRSc broth culture medium without phenol was used as a control. After incubating at 37° C. for 24 hours, the absorbance (A) OD630 nm was measured according to the following formula to evaluate the resistance to phenol.

Phenol tolerance (%)=$(A1/A0)\times 100$ wherein, $A_1$ is the absorbance of the culture after treatment, and $A_0$ is the absorbance of the culture before treatment. The results show that the strain of MSR101 has a good survival ability at a phenol concentration of 0.2% to 0.4%.

Example 4

Hemolytic Activity

*Lactobacillus* isolates were distributed in stripes on the surface of Columbia blood medium (Sigma, China) containing 5% sheep blood, and a plate was cultured at 37° C. for 72 hours. After incubation, the plate was checked for hemolytic activity.

The results show that the MSR101 strain has no hemolytic activity, thus it is safe in terms of hemolytic activity.

Example 5

Antibiotic Resistance

Figure 2:
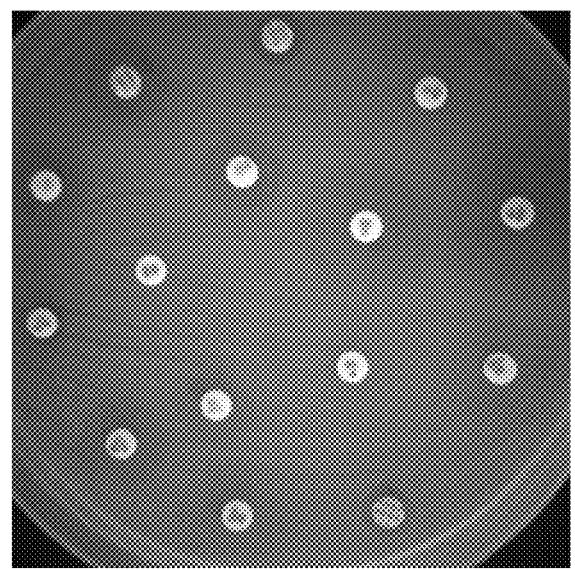
FIG. 2 is a diagram of the results for antibiotic resistance provided by the present disclosure.
Figure 3:
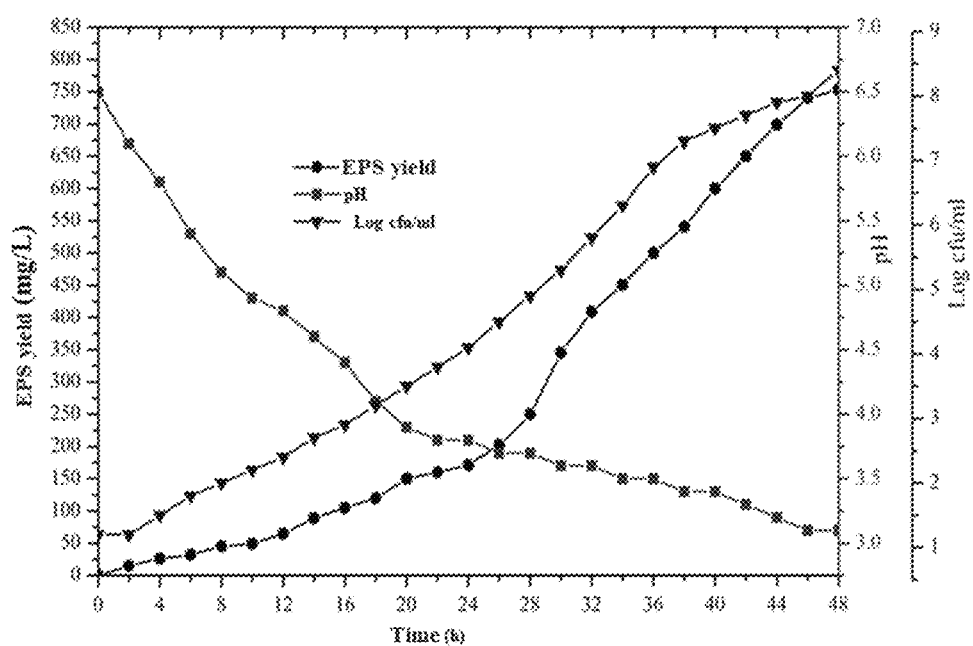
FIG. 3 is a diagram showing the yield of extracellular polysaccharides provided by the present disclosure.

The antibiotic resistance of *Lactobacillus* isolates was evaluated by the previously reported (Riaz Rajoka et al., 2017) agar overlap diffusion method. All *Lactobacillus* isolates were tested for resistance to 10 antibiotics, including penicillin, erythromycin, ampicillin, streptomycin, tetracycline, vancomycin, gentamicin, kanamycin, chloramphenicol and gram Linmycin. The method comprises the steps of covering the freshly prepared $MRS_c$ agar plate with 50 µl of active *Lactobacillus* culture, and incubating the plate at 4° C. for 1 h, placing an antibiotic disc on the plate, and incubating the plate at 37° C. for 24 h, then measuring the diameter of the suppressed zone. The results of antibiotic resistance are shown in FIG. 2 and Table 1. The *Lactobacillus kefiri* MSR101 is resistant to penicillin, ampicillin, streptomycin and tetracycline.

TABLE 1

| Antibiotic resistance | | | | | | | | | | |
|---|---|---|---|---|---|---|---|---|---|---|
| [057] Isolated strains of *Lactobacillus* | [058] enicillin | [059] rythro-mycin | [060] mpicillin | [061] trepto-mycin | [062] etra-cycline | [063] anco-mycin | [064] enta-micin | [065] ana-mycin | [066] hloram-phenicol | [067] linda-mycin |
| [068] MSR101 | [069] | [070] | [071] | [072] | [073] | [074] | [075] | [076] | [077] | [078] |

[01] (S) = susceptible and (R) = immune

Example 6

Production of Extracellular Polysaccharides

*Lactobacillus* cultures were grown in a flask containing freshly prepared 100 ml of $MRS_c$ broth supplemented with 3% (w/v) glucose, and incubated at 37° C. for 72 h. The bacterial cells were removed by centrifugation (7000×g, 10 min), and two volumes of pre-cooled ethanol were added to one volume of supernatant for precipitation of extracellular polysaccharides (EPS). The EPS precipitate was recovered by centrifugation (10000×g, 35 min) at 4° C., dialyzed (6000 Da to 8000 Da) for 48 h, and then lyophilized. Using glucose as a standard solution, the total amount of sugar was measured by a phenol-sulfuric acid method (Nikolic et al., 2012). Currently, the *L. kefiri* MSR101 strain producing EPS was originally isolated from the kefir grains in the Tibet Autonomous Region of Qinghai Province. The MSR101 strain showed a sticky appearance, which indicated that it was an EPS-producing strain. The *L. kefiri* MSR101 strain entered a stationary phase after 48 h of culture and the EPS amount reached a maximum value of 753 mg/L, and then entered the decline phase. The results showed that the MSR101 strain grew rapidly within 32 hours of culture, and the pH value of the medium dropped rapidly. After 48 h, the growth rate of the strain decreased, and the pH value of the medium dropped slightly. The pH value was about 3.1±0.5 at 48 h.

Example 7

Hydrophobicity to Cell Surface

Through the adhesion test of microorganisms to hydrocarbon compounds, the hydrophobicity of the cell surface of lactic acid bacteria was studied (Kotzamanidis et al., 2010). In short, the stationary phase cells were harvested by centrifugation (8000×g, 5 min), washed twice with PBS (pH7.2), and finally resuspended in PBS (pH7.2) to reach an OD of 0.6±0.02 at 630 nm ($A_0$). 1 ml of xylene was mixed with 1 ml of cell suspension, and allowed to stand at room temperature for 30 minutes to form a two-phase system. The water phase was carefully removed, and its absorbance ($A_1$) at 630 nm was measured. The cell surface hydrophobicity (%) is measured by the following formula:

Cell surface hydrophobicity (%)=$(1-A_1/A_0) \times 100$

*Lactobacillus kefiri* MSR101 strain shows high hydrophobicity (70%) to xylene which is a standard hydrocarbon for measuring the hydrophobicity of microbial cells.

Example 8

Antioxidant Activity
Preparation of Intact Cells
The overnight *Lactobacillus* culture (7000×g, 15 min at 4° C.) was centrifuged and the cells was washed three times with PBS (pH7.2), and finally re-suspend in PBS (pH7.2) to a final concentration of $1 \times 10^6$ cfu/ml, antioxidant analysis was conducted.
Superoxide Anion Scavenging Test
An improved pyrogallol auto-oxidation method (Re et al., 2014) was used to conduct the superoxide anion scavenging test. That was, a *Lactobacillus* cell suspension (100 μl) with a final concentration of $1 \times 10^6$ cfu/ml in PBS (pH 7.2), 900 μl of water and 2 ml of Tris-HCl buffer (pH 8.1) were quickly mixed. As a control, sterile distilled water was used instead of the *lactobacillus* cell suspension. 50 μmol/ml of pyrogallol solution was added and incubated for 1.0 min. The absorbance at 330 nm of the control group and the sample was measured to evaluate its autooxidation. The superoxide anion scavenging ability of the tested *lactobacillus* is calculated by the following formula:

Scavenging ability (%)=$(\Delta A_0 - \Delta A) \times 100 / \Delta A_0$

Where $\Delta A_0$ and $\Delta A$ are the auto-oxidation rates of pyrogallol before and after adding the sample and deionized water, respectively. The clearance rate of superoxide anion radical is 65.5%.
DPPH Free Radical Scavenging Activity
The DPPH free radical scavenging ability of *Lactobacillus* was measured by a previously reported method (Son et al., 2018). That was, three (3) ml of *Lactobacillus* cell suspension and 3 ml of 0.5 mM DPPH free radical ethanol solution were mixed, and incubated for 30 minutes in the dark at room temperature. After incubation, the reaction mixture was centrifuged (10000×g, 20 min at 4° C.), and the absorbance of the supernatant at 517 nm was measured. The DPPH scavenging capacity is calculated by the following formula:

Scavenging ability (%)=$(1 - OD_{Sample}/OD_{control}) \times 100$

Wherein $OD_{Sample}$ and $OD_{Control}$ are the absorbance of sample and distilled water, mixed with DPPH solution, respectively. The scavenging rate of *Lactobacillus kefiri* MSR101 on DPPH free radicals is 43.3%.

Example 9

Ability to Lower Cholesterol
The cholesterol absorption capacity of the isolated lactic acid bacteria was determined according to the previously reported method (Wang et al., 2012). Briefly, the *Lactobacillus* isolate of each species (1% v/v) was inoculated into 10 ml of freshly prepared $MRS_c$ broth medium containing 0.2% sodium thioacetate (Sigma, China), 0.3% bovine bile (Sigma, China) and 100 μl/ml water-soluble cholesterol (Sigma, China), each test tube was incubated at 37° C. for 24 h. The cells were removed by centrifugation (10,000×g, 35 min at 4° C.). The phthalaldehyde method used for measuring cholesterol (Rudel and Morris, 1973) was used to determine the amount of cholesterol in used broth and non-inoculated sterile broth. The cholesterol removal rate for the strain of *Lactobacillus kefiri* MSR101 was 26.2%.

Example 10

Determination of Adhesion
Dulbecco's modified Eagle's medium (DMEM) supplemented with 2 mM L-glutamine, 10% heat-inactivated fetal calf serum, 100 μg streptomycin/ml, 1% non-essential amino acids and 100 Ul was used, and HT-29 cells cultured in a cell culture flask. Subsequently, HT-29 cells were inoculated into a 24-well culture plate at a concentration of $2.5 \times 10^5$ cells/well, cultured for 3 days, and the medium was changed every day. The cells were incubated at 37° C. in a 5% $CO_2$ atmosphere. The overnight culture of the *lactobacillus* isolate was centrifuged, washed twice with PBS (0.1M, pH7.2), and re-suspended in the same buffer to an appropriate concentration of diluted solution (absorbance OD6300.2, about $2 \times 10^8$ CFU/ml). Then the bacterial cells were added to each cell well and incubated at 37° C. for 4 h. The cells was washed with PBS (0.1M, pH7.2) after incubation and lysed with 0.1% Triton X-100 solution. The cell lysate was serially diluted, spread on the $MRS_c$ agar plate and incubated at 37° C. for 3 days. The bacterial adhesion rate was calculated.

Adhesion rate %=(adhered bacteria/total added bacteria)×100

The highest adhesion rate of strain *Lactobacillus kefiri* MSR101 in HT-29 cells was 34.4%.

Example 11

Statistical Analysis
The values are given in average and standard deviation, measured in triplicate. Tukey's multiple comparison test showed significant difference in all tests (p<0.05), which was statistically significant.

Technical Effects

*Lactobacillus kefiri* MSR101 and its Probiotic Potential
*Lactobacillus* MSR101 was isolated from samples of Kefir product collected in the Tibet Autonomous Region of Qinghai Province, China. It is gram positive, catalase negative, rod-shaped and mesophilic. Based on the 16s rRNA gene sequence (GCTTGGCGTCGTGCTATACATGCAAGTCGAACGC GTTTCCGTTATTGATTTTAGAGTGTTGCATTTGAAT GATTTAACACGAAACGAGTGGCGA ACTGGT-GAGTAACACGTGGGTACCTGCCCTTGAAGTAGGG-GATAACA CTTGGAAACAGGTGCTAA TACCGTATAACAACCAAAACCACATGGTTT TGGTT-TAAAAGATGGCTTCGGCTATCACTTTAG-GATGGACCCGGGCG TATTAGCTTGT TGGTAAGGTAATGGCCTACCAAGGCAATGA-TACGTA GCCGACCTAGAGGGTAATCGGCCACAT-TGGGACTGAGACACGGCCC AAACTCCTACGG-GAGGCAGGTAGGGAATCTTCCACAATGGACGAAA GTCTGATGGAGCAACGCCGCGTGAGTGAT- GAAGGGTTTCGGCTCGT AAAACTCTGTTGTTGAGAAGAACAGGTGTCAGAGTAACTGTTGACATCTTGACGGTATCCAACCAGAAAGCCACGGCTAACTACGTGCCAGCAGCCGCGGTAATACGTAGGTGGCAAGCGTTGTCCGGATTTATTGGGCGTAAAGCGAGCGCAGGCGGTTCTTAGGTCTGATGTGAAAGCCTTCG GCTTAACCGAGAAGTGCATCGGAAACCAGGAGACTTGAGTGCAGA AGAGGACAGTGGAACTCCATGTGTAGCGGTGAAATGCGTAGATATAT GGAAGAACACCAGTGGCGAAGGCGGCTGTCTGGTCTGTAACTGACG CTGAGGCTCGAAAGCATGGGTAGCGAACAGGATTAGATACCCTGGT AGTCCATGCCGTAAACGATGAGTGCTAAGTGTTGGAGGGTTTCCGCCCTTCAGTGCTGCAGCTAACGCATTAAGCACTCCGCCTGGGGAGTAC GACCGCAAGGTTGAAACTCAAAGGAATTGACGGGGGCCCGCACAAG CGGTGAGCATGTGTTTAATTCGATGCTACGCGAAGACCTTACCAGGTCTTGACATCTTTCTCCTATTTCTGTCACCTTAGACGGCTGGTCCCCGA AGGTTA (SEQ ID NO: 1), the isolate was identified, and the obtained sequence is shown to be 99% similar to the sequence of the known species available in the NCBI database, which was deposited in the Gene Bank under the accession number of MK491609. The properties of probiotics were tested in terms of antibiotic sensitivity, tolerance under intestinal conditions (low pH, bile salt tolerance, and 0.2% to 0.4% resistance to phenol), hydrophobicity, antioxidant ability, cholesterol-lowering, and adhesion to HT-29, etc. The strain of the present disclosure is resistant to penicillin, ampicillin, streptomycin and tetracycline. In addition, it also exhibits adhesion (34.3%) to HT-29 cells and antioxidant activity (67%). The strain shows high survival rate (>80%) under gastrointestinal conditions, indicating their potential for probiotic applications (as shown in Table 2).

TABLE 2

| | Probiotic potential | | | | | | | | |
|---|---|---|---|---|---|---|---|---|---|
| | | | Phenol resistance | | Adhesion to HT-29 | | Antioxidant activity | | Ability to lower |
| Strain | Acid resistance | Bile tolerance | 0.2% | 0.4% | cells | Hydrophobicity | Superoxide anion scavenging test | DPPH | cholesterol |
| MSR101 | 75.4 ± 0.4% | 62.5 ± 0.1% | 81.2 ± 0.6% | 52.9 ± 0.3% | 34.4 ± 0.6% | 69.9 ± 0.1% | 65.5 ± 0.6% | 43.3 ± 0.3% | 26.2 ± 0.6% |

The description of the above embodiments is only used to help understand the method and core idea of the present disclosure. It should be pointed out that for those of ordinary skill in the art, several improvements and modifications can be made to the present disclosure without departing from the principle of the present disclosure, and these improvements and modifications also fall within the protection scope of the claims of the present disclosure. Various modifications to these embodiments are apparent to those skilled in the art, and the general principles defined herein can be implemented in other embodiments without departing from the spirit or scope of the present disclosure. Therefore, the present disclosure will not be limited to the embodiments illustrated in this document, but should conform to the widest scope consistent with the principles and novel features disclosed in this application.

What is claimed is:

1. A method for lowering concentration of cholesterol in a subject in need thereof, comprising a step of administering a strain of *Lactobacillus kefiri* MSR101 to the subject, wherein the strain of *Lactobacillus kefiri* MSR101 is deposited with the China General Microbiological Culture Collection under the accession number of CGMCC No. 17506, the strain of *Lactobacillus kefiri* MSR101 comprising a 16s RNA gene sequence of SEQ ID NO: 1, and primers used to amplify the 16s rDNA sequence are 5"-AGAGTTT-GATCCTGGCTC AG-3" (SEQ ID NO. 2) and reverse 5"-CCGTCAATTCCTTTGAGTTT-3" (SEQ ID NO. 3).

* * * * *